US00PP25096P2

(12) United States Plant Patent
Wezelenburg, Jr.

(10) Patent No.: US PP25,096 P2
(45) Date of Patent: Nov. 25, 2014

(54) ***CERCIDIPHYLLUM* TREE NAMED 'JWW3'**

(50) Latin Name: *Cercidiphyllum japonicum*
Varietal Denomination: JWW3

(71) Applicant: Jan-Willem Wezelenburg, Jr., Hazerswoude-Dorp (NL)

(72) Inventor: Jan-Willem Wezelenburg, Jr., Hazerswoude-Dorp (NL)

( * ) Notice: Subject to any disclaimer, the term of this patent is extended or adjusted under 35 U.S.C. 154(b) by 124 days.

(21) Appl. No.: 13/815,249

(22) Filed: Feb. 13, 2013

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Susan McCormick Ewoldt
(74) *Attorney, Agent, or Firm* — Penny J. Aguirre

(57) ABSTRACT

A new cultivar of *Cercidiphyllum japonicum*, 'JWW3', characterized by its broadly columnar to ovate plant habit, its young shoots that are red to greyed-red in color, and its foliage that emerges red and mature to yellow and yellow-green.

2 Drawing Sheets

Botanical classification: *Cercidiphyllum japonicum.*
Variety denomination: 'JWW3'.

BACKGROUND OF THE INVENTION

The present invention relates to a new and distinct cultivar of *Cercidiphyllum japonicum* and will be referred to hereafter by its cultivar name, 'JWW3'. 'JWW3' is a new cultivar of Katsuratree for use as an ornamental landscape plant.

The Inventor discovered the new cultivar, 'JWW3', as naturally occurring whole plant mutation in a seedbed at his nursery in Hazerswoude-Dorp, The Netherlands in May of 2010. The seedbed had been planted with seeds collected from unnamed plants of *Cercidiphyllum japonicum.*

Asexual propagation of the new cultivar was first accomplished by the Inventor using grafting in summer of 2010 in Hazerswoude-Dorp, The Netherlands. Asexual propagation by grafting has determined that the new cultivar is stable and reproduced true to type in successive generations.

SUMMARY OF THE INVENTION

The following traits have been repeatedly observed and represent the characteristics of the new cultivar as grown in Hazerswoude-Dorp, The Netherlands. These attributes in combination distinguish 'JWW3' as a unique cultivar of *Cercidiphyllum.*

1. 'JWW3' exhibits a broadly columnar to ovate plant habit.
2. 'JWW3' exhibits young shoots that are red to greyed-red in color.
3. 'JWW3' exhibits foliage that emerges red and mature to yellow and yellow-green.

The parent plants, unnamed plants of *Cercidiphyllum japonicum*, differ from 'JWW3' in having foliage that is purple-green when young and blue-green in color when mature, and in lacking red coloration on the young shoots. 'JWW3' can be most closely compared to other cultivars that have foliage with unique coloration; 'Rotfuchs' (syn. 'Red Fox', not patented) and 'Aureum' (not patented). 'Rotfuchs' differs from 'JWW3' in having foliage that is deep purple when young and matures to blue-green and in lacking red coloration on the young shoots. 'Aureum' is similar to 'JWW3' in having foliage that is yellow when mature, however 'Aureum' differs from 'JWW3' in having foliage that new growth that is purple-green in color, and in lacking red coloration on the young shoots.

BRIEF DESCRIPTION OF THE DRAWING

The accompanying colored photographs illustrate the overall appearance and distinct characteristics of a 2 year-old plant of the new cultivar as grown outdoors in a trial garden in Hazerswoude-Dorp, The Netherlands.

The photograph in FIG. 1 provides an overall view of the plant habit of 'JWW3'.

Figure 1:
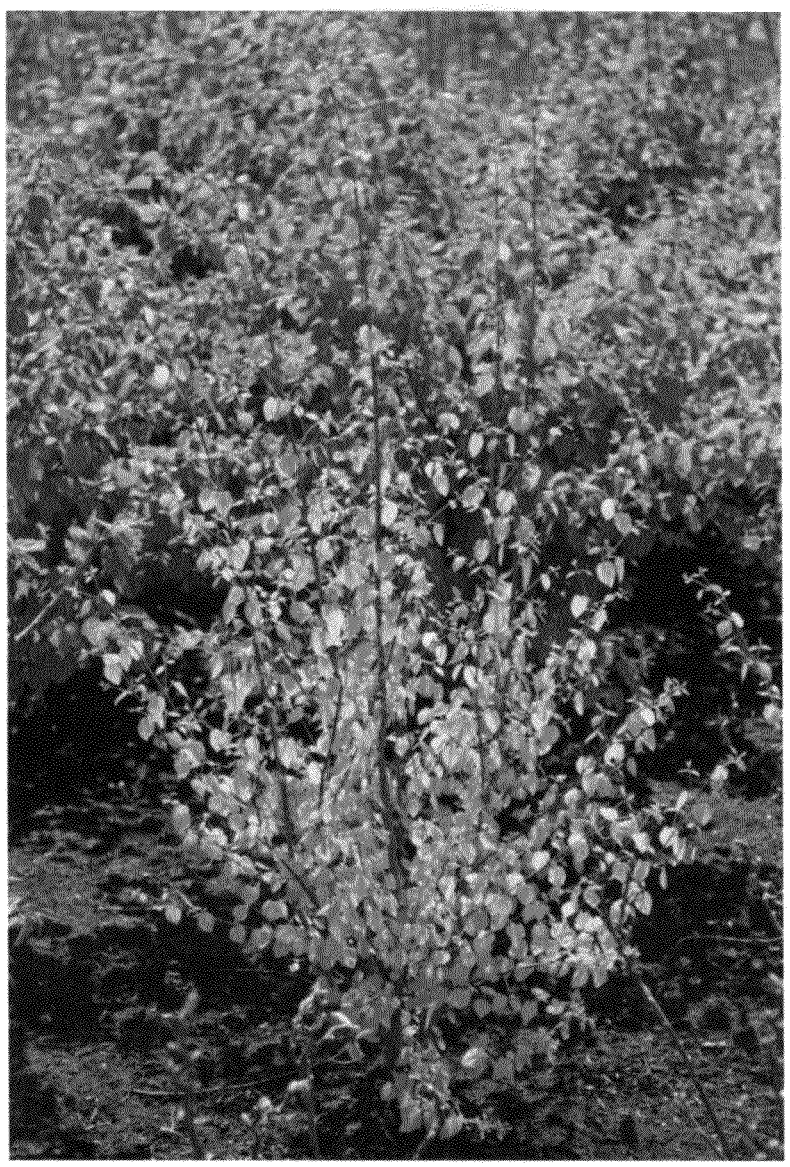
Figure 2:
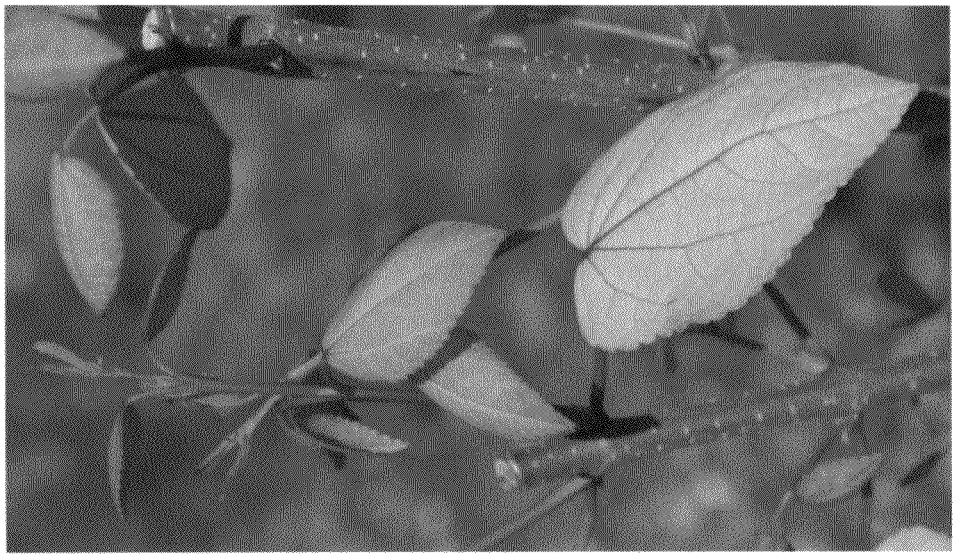
Figure 3:
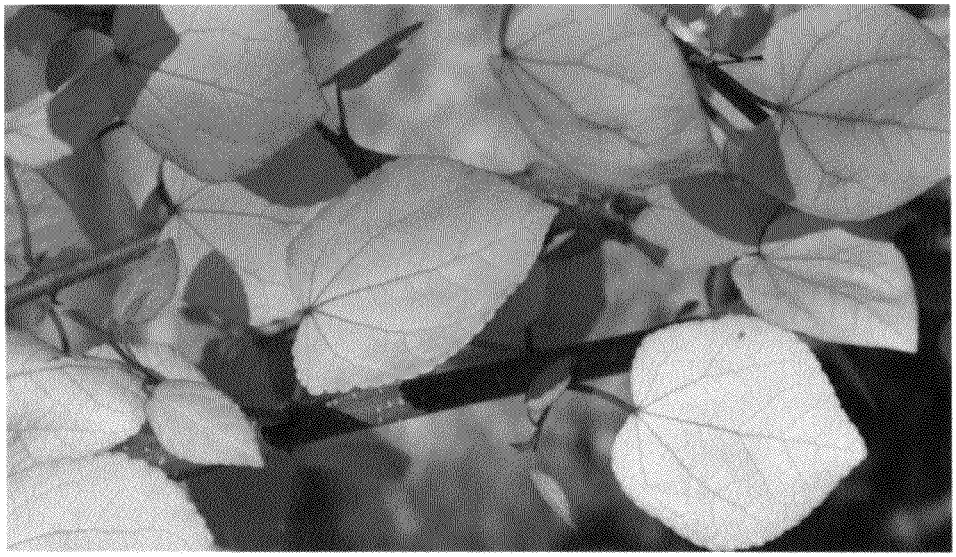

The photographs in FIG. 2 and FIG. 3 provide a close-up view of the foliage and young shoots of 'JWW3'. The colors in the photograph may differ slightly from the color values cited in the detailed botanical description, which accurately describe the colors of the new *Cercidiphyllum.*

DETAILED BOTANICAL DESCRIPTION

The following is a detailed description of 2 year-old plants of the new cultivar as grown in an unheated greenhouse in 19-cm containers in Hazerswoude-Dorp, The Netherlands. Plants were grown under average day temperatures ranging from 12° to 20° C. and average night temperatures of 6° to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Flowering have not been observed on the new cultivar.

*Plant type.*—Deciduous tree.

*Plant habit.*—Broadly columnar to ovate in shape.

*Plant size.*—Reaches about 44 cm in height and 24 cm in width as a 2 year-old plant.

*Hardiness.*—At least hardy to U.S.D.A. Zone 5.

*Environmental stress*.—Moderate to highly tolerant to wind and rain.

*Diseases and pests*.—No particular susceptibility or resistance to pests and diseases has been observed.

*Root description*.—Fibrous, moderately dense.

*Growth rate*.—Moderate.

Stem description:

*Shape*.—Round.

*Stem color*.—New growth; 41B and changing to 174A to 174B, mature wood; 197A to 197B.

*Stem size*.—An average of 28.3 cm in length and 3 mm in diameter, main trunk; about 3 cm in width as measured 5 cm from the soil level.

*Stem surface*.—Shoots smooth and glossy, mature wood slightly rough barked.

*Stem aspect*.—Rounded, in an average angle of 35° to main stem.

*Stem strength*.—Very strong.

*Branching*.—Free branching, an average of 5 lateral branches.

Foliage description:

*Leaf shape*.—Cordate.

*Leaf division*.—Simple.

*Leaf base*.—Cordate.

*Leaf apex*.—Broad acute.

*Leaf fragrance*.—In Autumn when leaves have dropped, they spread a pleasant "burnt sugar" like fragrance, typical for *Cercidiphyllum*.

*Leaf venation*.—Laciniate, color of upper surface; 144A, color of lower surface; 144B.

*Leaf margins*.—Crenate.

*Leaf arrangement*.—Opposite.

*Leaf attachment*.—Petiolate.

*Leaf surface*.—Both surfaces dull.

*Leaf internode length*.—An average of 3.6 cm.

*Leaf size*.—An average of 5.8 cm in length and 5.5 cm in width.

*Leaf quantity*.—An average of 16 (8 pairs).

*Leaf color*.—Immature upper and lower surface; between 31B and 179B, mature upper surface; 151C to 151D, mature lower surface; between 145C and 150B, fall color; same as summer coloration.

*Petioles*.—About 3.2 mm in length and 1.5 mm in width, color; 180B, smooth surface.

*Stipules*.—A small filiform is present on the upper side of the base of the petiole, 6 mm in length and 1 mm in width, cuneate base, narrow acute to cleft apex, color between 145D and 150D becoming a color between 180D and 181D at the tip.

Inflorescence/fruit description: No flowers or fruit have been observed to date, *Cercidiphyllum japonicum* flowers are typically small, green, and insignificant.

It is claimed:

1. A new and distinct cultivar of *Cercidiphyllum* tree named 'JWW3' as herein illustrated and described.

* * * * *